United States Patent [19]

Peterson et al.

[11] 4,246,188
[45] Jan. 20, 1981

[54] ARYLSULFONIC ACID BROMOPHENYL ESTERS, THEIR PREPARATION, AND THEIR USE AS FLAMEPROOFING AGENTS

[75] Inventors: Egon N. Peterson, Neunkirchen-Seelscheid; Hermann Richtzenhain, Much-Schwellenbach, both of Fed. Rep. of Germany

[73] Assignee: Dynamit Nobel Aktiengesellschaft, Troisdorf, Fed. Rep. of Germany

[21] Appl. No.: 947,902

[22] Filed: Oct. 2, 1978

Related U.S. Application Data

[63] Continuation of Ser. No. 660,953, Feb. 24, 1976, abandoned.

[30] Foreign Application Priority Data

Mar. 1, 1975 [DE] Fed. Rep. of Germany ....... 2508993

[51] Int. Cl.$^3$ ............................................ C07C 143/68
[52] U.S. Cl. .............................. 260/456 P; 568/637; 568/776; 568/72 G; 260/45.75; 260/45.75 B
[58] Field of Search ...................................... 260/456 P

[56] References Cited

U.S. PATENT DOCUMENTS

| | | | |
|---|---|---|---|
| 2,678,878 | 5/1954 | Stewart | 260/456 P |
| 2,949,482 | 8/1960 | Sims et al. | 260/456 P |
| 3,472,896 | 10/1969 | Seki et al. | 260/456 P |
| 4,022,812 | 5/1977 | Regeoud et al. | 260/456 P |

OTHER PUBLICATIONS

Takenabu et al., Chem. Abst., vol. 66, #65223g (1967).
Smith et al., Chem. Abst., vol. 62 #14572c (1965).
Slagh et al., J.A.C.S., vol. 72, p. 2801 (1950).

*Primary Examiner*—James H. Reamer
*Attorney, Agent, or Firm*—Sprung, Felfe, Horn, Lynch & Kramer

[57] ABSTRACT

Aryl sulfonic acid esters of the formula

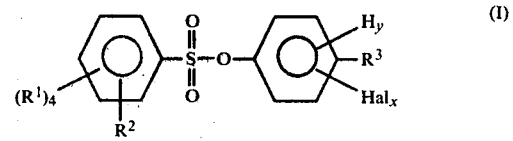

wherein $R^1$ represents hydrogen, alkyl groups of 1 to 8 carbon atoms, bromine or chlorine, $R^2$ represents $R^1$ or the group

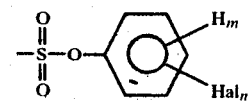

Hal represents bromine or chlorine, x the numbers 2 to 4, n the numbers 3 to 5, y the numbers $4-x$; $m=5-n$, $R^3$ represents bromine, chlorine or the group

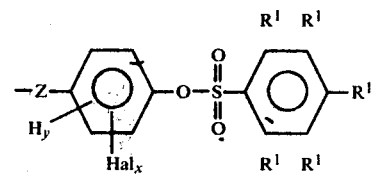

and Z represents —O—, —S—,

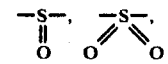

alkylene with 1 to 4 carbon atoms, or alkylidene; a process for their product and their use as a flame retardant, especially for polyolefins.

10 Claims, No Drawings

ARYLSULFONIC ACID BROMOPHENYL ESTERS, THEIR PREPARATION, AND THEIR USE AS FLAMEPROOFING AGENTS

This is a continuation of application Ser. No. 660,953 filed Feb. 24, 1976, now abandoned.

BACKGROUND

The invention relates to new arylsulfonic acid bromophenyl esters, aryldisulfonic acid-bis-(bromophenylesters) and bis-(arylsulfonic acid esters) of brominated bisphenols, their preparation and flameproof preparations of olefins containing these compounds as fire-retardants.

SUMMARY OF THE INVENTION

The new aryl mono- or disulfonic acid esters of highly brominated phenols have a structure of the general formula

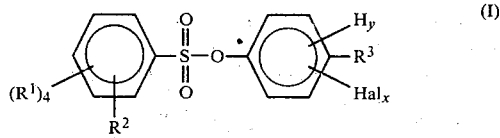

wherein $R^1$ represents hydrogen, alkyl groups of 1 to 8 carbon atoms, bromine, or chlorine, $R^2$ represents $R^1$ or the group

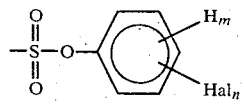

the expression Hal representing bromine or chlorine, x representing the numbers 2 to 4; y representing $4-x$, n the numbers 3 to 5 and m representing $5-n$, $R^3$ representing bromine, chlorine or the group

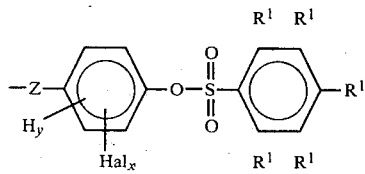

and Z representing —O—, —S—,

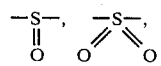

alkylene with 1 to 4 carbon atoms or alkylidene, such as —CH$_2$— or

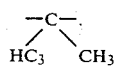

It is to be understood that the substituents $R^1$ on the same carbon ring can be identical or different, and that in the case of aryldisulfonic acid bis-esters, the sulfonic ester groups are not in the ortho position.

The substances of the invention are easily accessible through the reaction of a solution of the bromophenols in their phenols form in an appropriate solvent, with arylsulfonic acid chlorides, at normal or elevated temperature.

Hitherto, the only substances having a structure corresponding to Formula I which have been described in the literature either contain no halogen, or they contain chlorine, or else they are only weakly brominated, so that the arylsulfonic acid esters claimed in accordance with the invention are new substances. The following are examples of arylsulfonic acid components for the preparation of the substances of the invention: benzenesulfonyl chloride, alkyl- and especially methylbenzenesulfonyl chlorides such as o- or p-toluenesulfonyl chloride, benzene-1,3-disulfonyl chloride, chlorinated or, if desired, brominated benzenesulfonyl chlorides having 1 to 5 chlorine or bromine atoms, such as 2,3,4,5-tetrachlorobenzenesulfonyl chloride, and isomers or mixtures of isomers thereof, and similar compounds. The following can be used as bromophenols or brominated bisphenols: 2,4,6-tribromophenol, the isomeric tetrabromophenols or isomer mixtures, pentabromophenol, brominated p,p'-diphenylolalkyldienes such as tetrabromobisphenol A; 3,5,3',5'-tetrabromo-4,4'-dihydroxydiphenylsulfone, and others. Of these, in the case of the mononuclear bromophenols, those especially are preferentially suitable which contain at least three bromine atoms per aromatic nucleus and, in some cases, additional chlorine atoms. The reaction is performed with equivalent amounts, small excesses of one component being possible, i.e., one mole of phenol or one-half mole of bisphenol with each mole or arylsulfonyl chloride, and 2.0 moles of phenol with each mole or aryldisulfonyl chloride, in which case relatively low temperatures of 10° C. to about 80° C., and generally 20° C. to 60° C., are possible.

The solvents used need not be especially selected. Those which are miscible or partially miscible with water are desirable, such as low alcohols of 1 to 6 carbon atoms, glycols, and glycol ethers, and the like.

The substances of Formula I are very effective and advantageous flameproofing agents for polyolefins, i.e., polyethylene of high or low density, polypropylene, polybutylene, polymethylpentene, and others. They fulfill to a high degree the requirements which must be satisfied by a good flameproofing agent. They can easily be incorporated into polyolefins, they are well compatible with the polymers. They do not chalk out, and they are entirely stable thermally at the necessary fabrication temperatures.

Another advantage of the substances of the invention is that relatively small amounts suffice for the achievement of good flameproofing effect, while producing only slight alterations of the physical and mechanical properties of the finished products.

Still another considerable advantage is that the bromine content of the substances of Formula I need not be too high, in contrast to numerous conventional flameproofing agents. Thus it is generally unnecessary to select compounds in which the aromatic nucleus originating from the sulfonyl chloride is brominated, even though compounds brominated or chlorinated in this manner are entirely usable. Surprisingly, substances having three bromine atoms in the aromatic nucleus of the phenol radical, i.e., those containing only 40 to about 50 wt.-% bromine, produce a good flame inhibiting action, and in some cases produce as good a flame inhibiting action as more highly brominated compounds. Also, disulfonic acid esters of bisphenols having four bromine atoms divided between the two aromatic nuclei provide a good flame-inhibiting action in spite of a bromine content of less than 40% by weight. Since the bromine content is a substantial factor in the cost of flameproofing agents, on account of the high cost of bromine, the comparatively low bromine content of the substances of the invention and the simplicity of their production result in a technical and economic advantage.

The arylsulfonic acid esters of the present invention are used in the polymers together with synergetically acting compounds such as zinc borate, sodium antimonite, and, to special advantage, with antimony trioxide. The synergism with antimony trioxide is no pronounced that surprisingly low amounts of antimony trioxide produce good flame-inhibiting effects, making the arylsulfonic acid esters of the present invention superior, again, to other flame-proofing agents. Among the substances of the invention, the synergistic effect of benzenesulfonic acid tribromophenyl ester with antimony trioxide is especially advantageous.

In general, from 2 to 15 weight-percent of the arylsulfonic acid ester is used, from 3 to 10% being especially advantageous. Of the antimony trioxide, 0.3 to 8% is used, from 0.5 to 5 weight-percent being especially advantageous.

The incorporation of the flameproofing additives can be accomplished in a conventional manner by mixing on heated rollers, by mixing in an extruder, or by any other suitable method.

EXAMPLES

The following examples are intended to explain the invention and the methods of the invention, without limiting them.

The present invention is being described with reference to certain specific embodiments, and it is to be observed that modifications and variations can be made within the scope of the claims that follow. The invention can also be embodied in a technically different manner than described herein, without departing from the scope of the invention or from the idea thereof.

EXAMPLE 1—Preparation of benzenesulfonic acid-2,4,6-tribromophenyl ester (a) In ethanol as solvent In a two-liter reaction flask equipped with stirrer, dropping funnel and thermometer, 800 ml of 90% aqueous ethyl alcohol and 496.5 g (1.5 moles) of technical 2,4,6-tribromophenol were placed and mixed by stirring at room temperature with a solution of 60 g (1.5 moles) of sodium hydroxide in 60 ml of water, whereupon the tribromophenol went rapidly into solution with the formation of phenolate, and the mixture warmed of itself to about 32°–35° C.

The brownish phenolate solution obtained was cooled down to about 25° C., and then, with stirring, 265 g, equal to approximately 192 ml (1.5 moles) of benzenesulfonic acid chloride was added drop by drop over a period of 40 to 60 minutes such that the temperature of the mixture did not rise above 35° C.

The arylsulfonic acid ester precipitated soon in colorless needles in addition to sodium chloride.

After all of the sulfonyl chloride had been added, the mixture was stirred at about 30° C. for one hour, and then it was cooled to room temperature and the solids were removed with a suction filter. The filter cake was first washed with a little ethanol, and then the sodium chloride was washed out with water until there was no longer any chloride in the filtrate, and the ester was then dried. 638 g of arylsulfonic acid ester was obtained, corresponding to a yield of 90.5%. Melting point 82°–86° C.

(b) In ethylene glycol monomethyl ether (methyl cellosolve)

As under (a), in a similarly equipped 4-liter flask, 1,986 g (6 moles) of tribromophenol was suspended in 3.2 liters of water-containing methyl cellosolve (B.P. 117°–122° C.) and dissolved to form the phenolate by adding a solution of 240 g (6 moles) of sodium hydroxide in 240 ml of water.

Then, at a temperature between 25° and 35° C., 1,060 g = 768 ml (6 moles) of benzenesulfonyl chloride was stirred, drop by drop, into the phenolate solution. Sodium chloride and the sulfonic acid ester began to precipitate after the addition of about a third of the sulfonic acid chloride.

After all of the benzenesulfonyl chloride had been added, the reaction was completed at 35° C. in one hour, and then the crystalline mass was chilled to about 0° C., and the ester and sodium chloride were removed with a suction filter. The filter cake was stirred in 8 liters of water, the ester was suction filtered and washed free of sodium chloride. Then it was vacuum-dried at 50°–60° C.

2,665 g, corresponding to a 94.3% yield, of colorless needles melting at 83.5°–84.5° C. was obtained.

10 g of the raw ester was recrystallized from 30 ml of cyclohexane, or ethanol, or isopropanol. 8.7 g was obtained, having a melting point of 84.5°–86° C.

Elemental analysis: $C_{12}H_7Br_3O_3S$ (Mol. Wt. 470.98). Calculated: C 30.6%; H 1.5%; Br 50.95%; O 10.2%; S 6.8%. Found: C 30.49%; H 1.42%; Br 51.11%; O 10.32%; S 6.76%.

EXAMPLE 2—Preparation of pentabromophenylbenzenesulfonic acid ester

In the same apparatus as in Example 1, 488.7 g (1 mole) of pentabromophenol was suspended in 1.5 liters of methylcellosolve (B.P. 117°–122° C.), and was transformed to the phenolate by stirring into it a solution of 40 g (1 mole) of sodium hydroxide in 40 ml of water. To this phenolate solution, 177 g = 128 ml (1 mole) of technical benzenesulfonic acid chloride was added drop by drop in such a manner that the temperature of the reaction mixture did not rise above 35°–37° C.

The ester that formed began to precipitate together with sodium chloride after about half of the sulfonyl chloride had been added. After all of the benzenesulfochloride had been added, stirring was continued for 1 hour at 35° C. and the suspension was then cooled to room temperature.

The solids were suction filtered as in Example 1 and washed free of sodium chloride. After drying, we obtained 577 g, corresponding to 91.8% of the theoretically possible quantity of virtually colorless benzenesulfonic acid ester melting at 158°–160° C. (a residue at 170°–172° C.).

30 g of raw ester was recrystallized from benzene in a ratio of 1:4, or from xylene 1:4, or even methoxyethyl chloride 1:4, and colorless crystals melting at 171°–173° C. were thus obtained. 20 g of this product was once again recrystallized from 150 ml of a 1:1 mixture of cyclohexane and benzene, and yielded 14.9 g of pure crystallizate of a melting point of 172°–174° C.

Elemental analysis: $C_{12}H_5Br_5O_3S$ (Mol. wt. 628.8). Calc.: C 22.92%; H 0.80%; Br 63.54%; O 7.63%; S 5.10%. Found: C 23.11%; H 0.74%; Br 63.43%; O 7.63%; S 4.96%.

EXAMPLE 3—Preparation of a benzenesulfonic acid ester from a bromophenol containing chlorine in the nucleus For this experiment a halogen phenol mixture was used which had been obtained by the bromination of phenol with bromine chloride, and had the following gross composition:

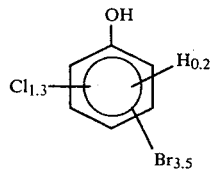

Bromine content: 67.5%
Chlorine content: 11.0%

By the procedure of Example 1, 123 g (about 0.3 moles) of halogen phenol of the above composition was suspended in 450 ml of ethyleneglycol monomethyl ether (B.P. 116°–121° C.) and dissolved to the phenolate by the addition of 12 g of sodium hydroxide in 12 ml of water.

At 30° C., it was then reacted to form the ester by adding, drop by drop, 53 g=38.4 ml (0.3 moles) of benzenesulfonyl chloride, the esterification being completed by allowing the reaction to continue for 45 minutes at 30° C.

After the precipitated material had been processed as described above, we obtained 153 g (98.5% yield) of benzenesulfonic acid halophenyl ester, M.P. 152°–154° C.

10 g of the raw ester, recrystallized from 60 ml of cyclohexane and benzene in a ratio of 2:1 by volume, yielded 9.3 g of colorless crystallizate of the same melting point of 152°–154° C.

In the same manner, by the reaction of a variously substituted halophenol of the gross composition $C_6H_y$-$Hal_x$—OH, wherein y=0.56, $Hal_x$=$Br_{4.33}$+$Cl_{0.11}$, with benzene-sulfonic acid chloride, the corresponding benzenesulfonic acid halophenyl ester was obtained in a 91% yield.

Elemental composition: $C_6H_5SO_2O$ $C_6H_{0.56}Br_{4.33}Cl_{0.11}$

EXAMPLE 4—Preparation of p-toluenesulfonic acid pentabromophenyl ester

In a one-liter three-necked flask equipped with stirrer and thermometer, there was placed 600 ml of methyl cellosolve (B.P. 117°–122° C.), and 345 g (0.5 moles) of pentabromophenol was suspended therein and dissolved to the phenolate by stirring in 20 g (0.5 moles) of sodium hydroxide dissolved in 20 ml of water.

At about 40° C., 95.4 g (0.5 moles) of p-toluenesulfonyl chloride in solid form was added in portions with vigorous stirring. Stirring was then continued for 1 hour at 40° C. and then, after cooling to room temperature, the precipitated solids were isolated as in Example 2.

We obtained 306 g (95.3% yield) of light brown raw ester melting at 192°–198° C. 15 g of raw ester, upon recrystallization from toluene in a ratio of 1:4 with the addition of animal charcoal, yielded 12 g of colorless crystallizate melting at 197.5°–200° C.

Elemental Analysis: $C_{13}H_7Br_5O_3S$ (Mol. wt. 642.8). Calc.: C 24.29%; H 1.10%; Br 62.16%; O 7.47%; S 4.99%. Found: C 24.38%; H 0.98%; Br 62.35%; O 7.36%; S 4.78%.

The o-toluenesulfonic acid pentabromophenyl ester can be prepared in the same manner by using the same molar amount of o-toluenesulfonyl chloride instead of the para compound.

EXAMPLE 5—p-Toluenesulfonic acid-2,4,6-tribromophenyl ester

This ester was prepared similarly to the preceding examples with the following quantities:

300 ml of methylcellosolve (B.P. 117°–122° C.)
165.5 g (0.5 mole) of 2,4,6-tribromophenol,
20 g (0.5 mole) of sodium hydroxide in 20 ml water,
95.4 g (0.5 mole) of p-toluenesulfonyl chloride.

Raw ester yield: 221 g, corresponding to 91%. Melting point: 112°–113.5° C. After recrystallization from cyclohexane in a ratio of 1 g of ester to 6 ml of solvent, the melting point was 113°–114.5° C.

Elemental analysis: $C_{13}H_9Br_3O_3S$ (mol. wt. 485.06). Calc.: C 32.22%; H 1.86%; Br 49.40%; O 9.90%; S 6.62%. Found: C 32.38%; H 1.73%; Br 49.63%; O 9.98%; S 6.71%.

In the same manner the o-toluenesulfonic acid-2,4,6-tribromophenyl ester can be obtained by using o-toluenesulfonyl chloride in the same molar amount instead of the para compound.

EXAMPLE 6—2,3,4,5-tetrachlorobenzenesulfonic acid-2,4,6-tribromophenyl ester

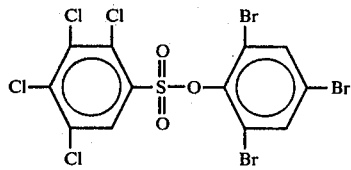

In preparing this sulfonic acid ester a sulfonyl chloride was used which had been obtained by the reaction of chlorosulfonic acid with "tetra oil", a by-product occurring in the production of hexachlorocyclohexane.

Tetra oil is a mixture of chlorinated benzenes, and it is composed as follows:

0.4% 1,2,3-trichlorobenzene
8.3% 1,2,4-trichlorobenzene
13.9% 1,2,4,5-tetrachlorobenzene
65.1% 1,2,3,4-tetrachlorobenzene, and
12.3% pentachlorobenzene.

By fractional distillation we obtained the 1,2,3,4-tetrachlorobenzene in a purity of about 95%, and from that we obtained the sulfochloride with a melting point of about 70° C. in a 76% yield.

In the apparatus already described, 82.7 g (0.25 mole) of technical 2,4,6-tribromophenol was suspended in 250 ml of methyl glycol (B.P. 122°–126° C.) and converted to the phenolate with a lye prepared from 10 g (0.25 mole) of sodium hydroxide in 10 ml of water. At 35° C., 78.6 g (0.25 mole) of 2,3,4,5-tetrachlorobenzenesulfonyl chloride was then stirred in portion-wise such that the temperature in the reaction mixture did not exceed 40° C. A fine, white precipitate formed.

We let the reaction continue for one hour at 60° C., and then cooled the mixture to room temperature and removed the precipitate with a suction filter. The precipitate was washed chloride-free with water and dried.

Yield: 128 g (84%) M.P. 162°–166° C.

10 grams, when recrystallized from 50 ml of methylcellosolve, had a melting point of 164°–167° C. Repeated recrystallization did not change the melting point.

Elemental analysis: $C_{12}H_3Br_3Cl_4O_3S$ (mol. wt. 308.76). Calc.: C 23.69%; H 0.50%; Br 39.38%; Cl 23.29%; O 7.88%; S 5.26%. Found: C 23.83%; H 0.46%; Br 39.50%; Cl 23.16%; O 8.01%; S 5.34%.

EXAMPLE 7—m-Benzenedisulfonic acid-bis-(2,4,6-tribromophenyl ester)

By the procedure described above, 331 g (1.0 mole) of tribromophenol was suspended cold in 500 ml of methyl glycol having a boiling point of 117°–122° C., and converted to the phenolate by the addition of a solution of 40 g (1.0 mole) of sodium hydroxide in 40 ml of water.

A solution of 138 g (0.5 mole) of technical benzene-1,3-disulfochloride, dissolved in 350 ml of methyl glycol, was added drop by drop to the phenolate solution, whereupon a white precipitate immediately formed. A thickish suspension formed, which, after the addition of all of the sulfochloride, was stirred for another hour at 40° C.

After the mixture had cooled to room temperature, the precipitate was suction filtered, washed free of sodium chloride, and dried.

Yield: 358 g (83%) of raw, colorless disulfonic acid ester melting at 163° to 168° C.

After two recrystallizations of 20 grams from 200 ml of a mixture of benzene and cyclohexane in a ratio of 3:2 by volume, the melting point was 172°–175° C.

Elemental analysis: $C_{18}H_8Br_6O_6S_2$ (mol. wt. 863.84). Calculated: C 25.03%; H 0.93%; Br 55.50%; O 11.11%; S 7.42%. Found: C 25.14%; H 0.91%; Br 55.32%; O 11.23%; S 7.31%.

EXAMPLE 8—m-Benzenedisulfonic acid-bis-(pentabromophenyl ester)

By the same procedure as in Example 7,
50 ml of methylcellosolve,
48.9 g (0.1 mole) of pentabromophenol,
4.0 g (0.1 mole) of sodium hydroxide, dissolved in 4 ml of water, and
13.8 g (0.05 mole) of benzene-1,3-disulfonylchloride, dissolved cold in 50 ml of methylcellosolve, was brought to reaction, the solution of the disulfonyl chloride being added drop by drop to the phenolate solution, with stirring, over a period of about 20 minutes at 30° C. The stirring was then continued for an additional hour at 30° C.

After the mixture had cooled to room temperature, the suspension was suction filtered and the bis-ester was washed free of sodium chloride with water. After drying we obtained 52.5 g (89% yield) melting at 248°–255° C.

10 g of the raw ester was recrystallized from 100 ml of xylene. We obtained a colorless crystallizate melting at 253°–256° C. The substance is furthermore soluble in dioxane and o-dichlorobenzene, for example.

Elemental analysis: $C_{18}H_4Br_{10}O_6S_2$ (mol. wt. 1,179.45). Calc.: C 18.33%; H 0.34%; Br 67.75%; O 8.14%; S 5.44%. Found: C 18.46%; H 0.31%; Br 67.62%; O 7.99%; S 5.47%.

EXAMPLE 9—Preparation of tetrabromobisphenol-A-bis(benzenesulfonic acid ester)

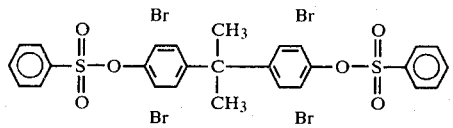

(a) In water

As described in the preceding examples, 2.040 g (3.75 moles) of technical tetrabromobisphenol A (i.e., 3,5,3',5'-tetrabromo-4,4'-dihydroxy-2,2-diphenylpropane) was suspended in 6 liters of water and dissolved to form the phenolate in a solution of 300 g (7.5 moles) of sodium hydroxide in 300 ml of water. At 25° C., 1,325 g=960 ml (7.5 moles) of benzenesulfonyl chloride was added to this solution drop by drop, with vigorous stirring, the ester settling out immediately as a colorless precipitate. After all of the benzenesulfonyl chloride had been added, we continued stirring for 30 minutes at room temperature. The ester was then suction filtered, washed free of chloride and dried. 2,850 g (92.2% yield) melting at 196°–205° C. was obtained.

(b) In methylcellosolve

In the manner described under (a), the following were reacted at 40° C. and processed as described:
2,040 g (3.75 moles) of tetrabromo-bisphenol A,
6 liters of methylcellosolve (B.P. 116°–121° C.),
300 g (7.5 moles) of NaOH in 300 ml of water, and
1,325 g=960 ml (7.5 moles) of benzenesulfonyl chloride. 2,996 g (96.9%) of raw ester was obtained, M.P. 196.5°–204° C. 20 g of the raw ester was recrystallized from 200 ml of a mixture of xylene and cyclohexane in a ratio of 3:2 by volume, yielding a colorless crystallizate melting at 204°–206° C.

Elemental analysis: $C_{27}H_{20}Br_4O_6S_2$ (mol.wt. 824.22). Calc.: C 39.35%; H 2.45%; Br 38.78%; O 11.65%; S 7.78%. Found: C 39.41%; H 2.34%; Br 38.91%; O 11.50%; S 7.66%.

In like manner, the tetrabromobisphenol-A-bis-(o-toluenesulfonic acid ester) and the -bis-(p-toluenesulfonic acid ester) are obtained by reacting o- and p-toluenesulfonic acid chloride, respectively, instead of benzenesulfonic acid chloride, with the bisphenol.

EXAMPLE 10—Preparation of 3,5,3',5'-tetrabromo-4,4'-dihydroxydiphenylsulfone-bis-(benzene sulfonate)

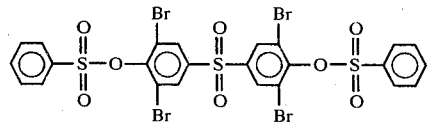

In the manner described in the preceding examples, the following were reacted
141.5 g (0.25 moles) of tetrabromodihydroxydiphenylsulfone, M.P. 285°–292° C.
1 liter of methylcellosolve 20 g (0.5 mole) of NaOH in 20 ml of water, and 88.3 g=64 ml (0.5 mole) of benzenesulfonyl chloride.

The benzenesulfonic acid chloride was added drop by drop over a period of 15 minutes at 30° C. The mixture was worked up as repeatedly described in the previous examples.

We obtained 176 g of raw ester, corresponding to a yield of 83%. The melting point was found at 184°-188° C. Upon recrystallization from xylene 1:6 we obtained colorless needles melting at 187°-190° C.

Elemental analysis: C$_{24}$H$_{14}$Br$_4$O$_8$S$_3$ (mol. wt. 846·21). Calc.: C 34.07%; H 1.67%; Br 37.77%; O 15.13%; S 11.37%. Found: C 34.18%; H 1.53%; Br 37.59%; O 15.04%; S 11.42%.

EXAMPLE 11—Preparation of 3,5,3',5'-tetrabromo-4,4'-dihydroxy-2,2-diphenylpropane-bis-(2,3,4,5-tetrachlorobenzene sulfonate)

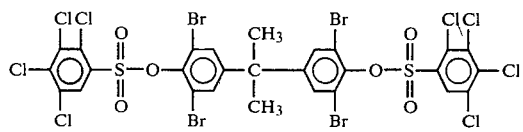

By the same procedure as already described, 108.8 g (0.2 mole) of technical tetrabromobisphenol A was suspended cold in 600 ml of methylcellosolve and dissolved to the phenolate by the addition of 16 g (0.4 mole) of sodium hydroxide in 16 ml of water. 125.8 g (0.4 mole) of tetrachlorobenzenesulfonyl chloride—prepared as in Example 6—was stirred into this solution at 40° C., and this reaction mixture was reacted three hours at 70° C. with stirring. Then the suspension that had been formed was cooled to room temperature and worked up as previously described.

We obtained 191 g (87%) of raw ester, M.P. 214°-240° C. After recrystallization 1:24 from ethylene glycol-monobutyl ether, M.P. 241°-247°.

Elemental analysis: C$_{27}$H$_{12}$Br$_4$Cl$_8$O$_6$S$_2$ (mol. wt. 1,099.8). Calc.: C 29.49%; H 1.10%; Br 29.06%; Cl 25.79%; O 8.73%; S 5.92%. Found: C 29.61%; H 1.04%; Br 29.18%; Cl 25.59%; O 8.66%; S 5.81%.

EXAMPLE 12

This example demonstrates the use of the compounds of the present invention as flameproofing agents for polyolefins.

The good thermal stability of the substances of the invention is apparent, for example, from the values obtained in the thermoanalytic determination of weight losses. The following, for example, were obtained with the benzenesulfonic acid esters of the tribromophenol from Example 1, in air, at a warming rate of 8° C. per minute:

| Weight Losses | | |
|---|---|---|
| 1% at 256° C. | 5% at 282° C. | 10% at 290°C. |

With the substance of Example 9, we found the following:

| Weight Losses | | |
|---|---|---|
| 1% at 281° C. | 5% at 293° C. | 10% at 301° C. |

The following table shows the test results for the degree of flame resistance based on the oxygen index testing of numerous samples containing various substances of the invention.

The values given under LOI vol.-% O$_2$ were determined in accordance with ASTM D 2863-70. They refer to the concentration of oxygen, expressed in volume-percent of an oxygen-nitrogen mixture which can barely sustain the combustion of the sample under the conditions of the experiment. The greater the oxygen index is, the better is the flame-inhibiting action of the formulation.

The incorporation of the flameproofing agents into the polyolefins was performed in a roller mixer. The roller skins obtained were then pressed to form the test strips.

TABLE

| | | | Amount of the flame proofing agent | | |
|---|---|---|---|---|---|
| Mixture | Polyolefin | Substance of Example No. | Ester | Sb$_2$O$_3$ | LOI Vol % O$_2$ |
| Example or Comparison | PA | — | — | — | 10.5 |
| Example or Comparison | PA | octabromodiphenyl ether | 9 g | 4 g | 27.2 |
| 1 | PA | 1 | 12 g | 5 g | 30.3 |
| 2 | PA | 1 | 12 g | 2 g | 29.6 |
| 3 | PA | 1 | 9 g | 3 g | 27.7 |
| 4 | PA | 1 | 9 g | 4 g | 27.6 |
| 5 | PA | 1 | 9 g | 3 g | 28.6 |
| 6 | PA | 1 | 9 g | 2 g | 28.3 |
| 7 | PA | 1 | 9 g | 1 g | 27.2 |
| 8 | PA | 1 | 9 g | — | 19.4 |
| 9 | PA | 1 | 6 g | 3 g | 27.4 |
| 10 | PA | 1 | 6 g | 2 g | 27.2 |
| 11 | PA | 1 | 3 g | 2 g | 21.8 |
| 12 | PP | — | — | — | 17.3 |
| 13 | PP | 1 | 12 g | 6 g | 27.3 |
| 14 | PP | 1 | 12 g | 4 g | 26.6 |
| 15 | PP | 1 | 12 g | 2 g | 25.1 |
| 16 | PP | 1 | 9 g | 4 g | 25.5 |
| 17 | PP | 1 | 9 g | 3 g | 25.1 |
| 18 | PP | 1 | 9 g | 2 g | 24.5 |
| 19 | PP | 1 | 6 g | 3 g | 24.5 |

TABLE-continued per 100 grams of polyolefin. PA = polyethylene PP = polypropylene

| Mixture | Polyolefin | Substance of Example No. | Amount of the flame proofing agent Ester | $Sb_2O_3$ | LOI Vol % $O_2$ |
|---|---|---|---|---|---|
| 20 | PP | 1 | 6 g | 2 g | 24.1 |
| 21 | PA | 2 | 12 g | 6 g | 28.3 |
| 22 | PA | 2 | 12 g | 5 g | 28.0 |
| 23 | PA | 2 | 12 g | 4 g | 27.9 |
| 24 | PA | 2 | 12 g | 2 g | 27.7 |
| 25 | PA | 2 | 9 g | 4 g | 25.8 |
| 26 | PA | 3 | 12 g | 5 g | 39.0 |
| 27 | PA | 3 | 12 g | 2 g | 29.3 |
| 28 | PA | 4 | 12 g | 5 g | 29.4 |
| 29 | PA | 4 | 12 g | 4 g | 29.4 |
| 30 | PA | 4 | 12 g | 2 g | 29.0 |
| 31 | PA | 4 | 9 g | 4 g | 29.5 |
| 32 | PA | 4 | 9 g | 2 g | 28.8 |
| 33 | PA | 4 | 9 g | — | 19.3 |
| 34 | PA | 4 | 6 g | 4 g | 27.7 |
| 35 | PA | 4 | 6 g | 2 g | 27.2 |
| 36 | PA | 6 | 12 g | 6 g | 27.6 |
| 37 | PA | 6 | 12 g | 4 g | 27.2 |
| 38 | PA | 6 | 12 g | 2 g | 26.9 |
| 39 | PA | 6 | 9 g | 4 g | 26.5 |
| 40 | PA | 6 | 9 g | 3 g | 26.4 |
| 41 | PA | 6 | 9 g | 2 g | 26.2 |
| 42 | PA | 6 | 6 g | 3 g | 23.6 |
| 43 | PA | 6 | 6 g | 2 g | 23.4 |
| 44 | PA | 7 | 12 g | 6 g | 29.7 |
| 45 | PA | 7 | 9 g | 4 g | 27.8 |
| 46 | PA | 7 | 9 g | 2 g | 26.4 |
| 47 | PA | 8 | 12 g | 5 g | 28.7 |
| 48 | PA | 8 | 9 g | 4 g | 27.2 |
| 49 | PA | 8 | 9 g | 2 g | 26.4 |
| 50 | PA | 9 | 12 g | 6 g | 29.5 |
| 51 | PA | 9 | 12 g | 4 g | 30.1 |
| 52 | PA | 9 | 12 g | 2 g | 29.8 |
| 53 | PA | 9 | 9 g | 4 g | 29.5 |
| 54 | PA | 9 | 9 g | 3 g | 29.1 |
| 55 | PA | 9 | 9 g | 2 g | 28.6 |
| 56 | PA | 9 | 6 g | 3 g | 27.6 |
| 57 | PA | 9 | 6 g | 2 g | 26.9 |
| Example or Comparison | PA | Octabromodiphenyl ether | 12 g | 4 g | 27.3 |
| Example or Comparison | PA | Octabromodiphenyl ether | 12 g | 2 g | 26.4 |
| Example or Comparison | PA | Octabromodiphenyl ether | 9 g | 4 g | 27.3 |
| Example or Comparison | PA | Octabromodiphenyl ether | 9 g | 2 g | 26.3 |
| Example or Comparison | PA | Octabromodiphenyl ether | 6 g | 4 g | 26.9 |
| Example or Comparison | PA | Octabromodiphenyl ether | 6 g | 2 g | 26.0 |

The table clearly shows the superiority of the action of the substances of the present invention in comparison with common commercial flameproofing agents. In the specimens containing the new substances there are many oxygen index values above about 27, which cannot be achieved at all with many of the prior-art substances, or only by the incorporation of amounts which impair the characteristics of the polyolefins. It is remarkable that good results are obtained with samples of the substance of Example 1 containing only three bromine atoms per molecule; also noteworthy is the particularly strong synergism of the $Sb_2O_3$ and the good oxygen index obtainable in this case with small contents of $Sb_2O_3$. Especially mixtures Nos. 5, 6 and 52 show the pronounced synergism with antimony trioxide, the amount of which can be surprisingly small. How conspicuous this synergism is is shown by Mixtures Nos. 8 and 33, which were prepared without $Sb_2O_3$.

We claim:

1. Aryl disulfonic acid esters of polybrominated phenols of the general formula

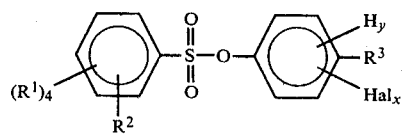

wherein $R^1$ represents hydrogen, alkyl groups of 1 to 8 carbon atoms, bromine or chlorine, $R^2$ represents $R^1$ or the group

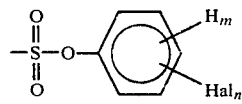

Hal represents bromine or chlorine,
x the number 2 to 4,
n the numbers 3 to 5,
y the numbers 4−x,
m=5−n,
$R^3$ represents the group

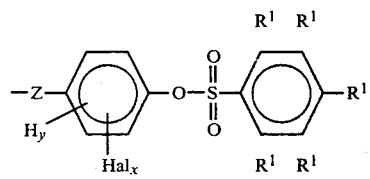

and Z represents —O—, —S—,

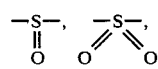

alkylene with 1 to 4 carbon atoms, or alkylidene.

2. An aryl disulfonic acid ester according to claim 1 wherein Z represents alkylene with 1 to 4 carbon atoms or alkylidene.

3. m-Benzenedisulfonic acid bis-(2,4,6-tribromophenyl ester.

4. m-Benzenedisulfonic acid bis-(pentabromophenyl ester.

5. Tetrabromobisphenol A bis-(benzenesulfonic acid ester).

6. Tetrabromobisphenol A bis-(o- and/or p-toluenesulfonic acid ester).

7. 3,5,3′,5′-Tetrabromo-4,4′-dihydroxydiphenylsulfone bis-(benzenesulfonic acid ester).

8. Tetrabromobisphenol A bis-(2,3,4,5-tetrachlorobenzenesulfonic acid ester).

9. An arylsulfonic acid ester according to claim 1 wherein $R^2$ is hydrogen, a $C_{1-8}$ alkyl group, bromine or chlorine.

10. An arylsulfonic acid ester according to claim 1 wherein $R^2$ is a group

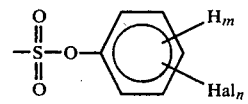

wherein Hal is bromine or chlorine, n is a number of 3 to 5 and m is (5−n).

* * * * *